United States Patent
Okazaki et al.

(10) Patent No.: US 6,930,198 B2
(45) Date of Patent: Aug. 16, 2005

(54) METHOD FOR PRODUCTION OF UNSATURATED CARBOXYLIC ESTER

(75) Inventors: Kazuto Okazaki, Himeji (JP); Yukihiro Matsumoto, Kobe (JP); Kazuhiko Sakamoto, Himeji (JP); Yuji Miyahara, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 257 days.

(21) Appl. No.: 10/132,529

(22) Filed: Apr. 24, 2002

(65) Prior Publication Data

US 2002/0169338 A1 Nov. 14, 2002

(30) Foreign Application Priority Data

May 14, 2001 (JP) ........................................ 2001-143340

(51) Int. Cl.⁷ .............................................. C07C 69/52
(52) U.S. Cl. ...................................................... 560/205
(58) Field of Search ........................................... 560/205

(56) References Cited

U.S. PATENT DOCUMENTS 5,892,103 A    4/1999  Sogabe et al.

FOREIGN PATENT DOCUMENTS

JP    A-10-231275    12/1996

*Primary Examiner*—Paul A. Zucker
(74) *Attorney, Agent, or Firm*—Mathews, Shepherd, McKay & Bruneau, P.A.

(57) ABSTRACT

A method for producing an unsaturated carboxylic ester is provided, which can prevent the raw material compounds and the product of the reaction from splashing and adhering on the inner wall of the reaction vessel and succumbing to polymerization on the inner wall. Specifically, it is characterized by the fact that the difference between the outer periphery of the reaction vessel heated by the heating means and the reaction solution in temperature is not higher than 80° C.

8 Claims, 1 Drawing Sheet

FIGURE
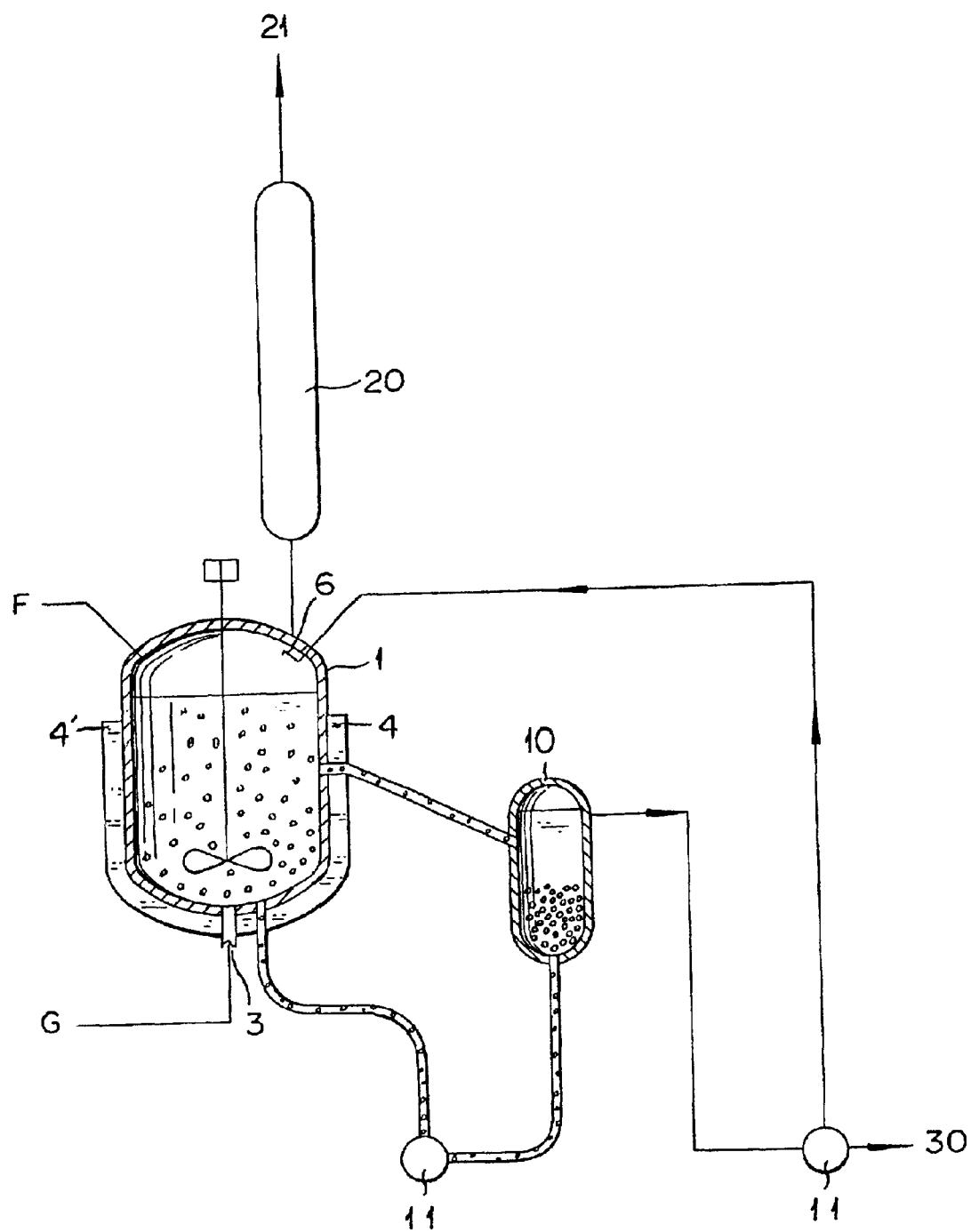

METHOD FOR PRODUCTION OF UNSATURATED CARBOXYLIC ESTER

BACKGROUND OF THE INVENTION

1. Field of the Invention

This invention relates to a method for the production of an unsaturated carboxylic ester from a corresponding unsaturated carboxylic acid and an aliphatic alcohol and more particularly to a method for the production of an unsaturated carboxylic ester which is enabled, by controlling the temperature of a heat source supplied from a heating means and the temperature of a reaction solution in respectively prescribed ranges, to prevent a polymerization on account of a raw material compound.

2. Description of the Related Art

In the production of an ester from an unsaturated carboxylic acid and an alcohol, the reaction vessel for use in the production is equipped with a heating means generally because the relevant reaction is enhanced by heating the reaction solution. In the method for producing an ester from an unsaturated carboxylic acid and an alcohol, the esterification is prevented from proceeding fully satisfactorily and the conversion ratio is lowered because of by-produced water. For this reason, the reaction solution requires to purge itself of the by-produced water contained therein. A method which consists in expelling the by-produced water from the reaction solution by means of a distillation column in order to shift the reaction equilibrium toward the reaction side and increase the conversion ratio is now available. In execution of this method, the reaction solution must be heated so as to retain in a boiling state and the reaction vessel must be furnished with a heating means.

Generally, the fact that the heating temperature is high is at an advantage in reducing the cost of equipment and the cost of labor because of decreasing the heating surface area and curtailing the temperature increasing time. Thus, a method which consists in relying on a heating means such as a heating jacket which is capable of covering the outer periphery of the reaction vessel to supply a heating medium having a higher temperature than the target temperature of the reaction solution thereby heating the reaction solution in the reaction vessel to a prescribed temperature has been finding in extensive utility.

Some of the reactions of esterification are catalyzed by the use of an ion-exchange resin. Particularly when the ion-exchange resin is uniformly dispersed in the reaction solution for the purpose of promoting the reaction of esterification, the ion-exchange resin is kept stirred by means of an agitating element equipped in the reaction vessel with the aim so as to proceed the reaction of esterification advantageously. To recover the product of the reaction which has been performed as described above, it becomes necessary to separate the ion-exchange resin from the reaction solution. Thus, a resin separating tank is adjoined to the reaction vessel and operated so as to introduce the reaction solution containing the product of the esterification and the ion-exchange resin, and keep the solution containing the resin standing at rest. The reaction vessel is operated meanwhile to permit circulation of the slurry containing the ion-exchange resin to the reaction vessel for the purpose of ensuring continuation of the manufacture of the product of the esterification. As a measure to attain this continued manufacture, the official gazette of JP-A-10-231,275, for example, discloses a method which reacts a carboxylic acid with an alcohol in a suspension of a strong acidic cation-exchange resin as a catalyst, introduces slurry reaction solution containing the ion-exchange resin into a resin separating tank, separates the slurry reaction solution into a clear liquid part and a slurry thick liquid part in the resin separating tank, and subsequently withdraws the clear liquid through the upper part of the resin separating tank and meanwhile withdraws the slurry thick liquid through the lower part of the resin separating tank in order to circulate the resin to the reaction vessel. When the ascending speed of the clear liquid based on the cross section of the resin separating tank is set below a specific level, the clear liquid which is obtained by this method either contains substantially no ion-exchange resin or contains the ion-exchange resin only in a markedly lowered concentration. Besides, it is claimed that this method, by an additional measure of causing a pipe extending from the reaction vessel to the resin separating tank to be connected to the lower half part of the separating tank at an angle in the range of 20–70° C. relative to the horizontal line, is enabled to avoid disturbing the flow of the liquid near the inlet of the separating tank and inducing flotation of the ion-exchange resin and allow easy separation of the slurry reaction solution into the slurry thick liquid and the clear liquid.

When the unsaturated carboxylic acid happens to be a compound such as an acrylic acid which has a polymerizable unsaturated double bond, however, there may arise the possibility that the heating means equipped on the outer periphery of the reaction vessel will excessively heat the outer wall of the reaction vessel and will consequently induce formation of a polymer on the inner wall of the reaction vessel. Particularly when an ion-exchange resin is used as a catalyst for the reaction, there may arise the possibility that the stirring of the reaction solution for the purpose of uniformly mixing the resin with the reaction solution will cause the splashing on the inner wall of the reaction vessel with the reaction solution, and polymerization. This adhesion of the polymer may possibly cause a loss in the raw material compound and the target product. When the ester is continuously produced, therefore, the adhered polymer results in inducing a large decline of the yield of the product. The polymer further impairs the flow of the liquid in the pipe, blocks the pipe, and entails the necessity of periodically suspending the operation of the apparatus for production and purging the reaction vessel and the pipes of the polymer adhering to their interiors.

When the resin separating tank is additionally installed as a means for the separation of the ion-exchange resin, it is preferred to have a pipe interconnect the bottom of the resin separating tank and the reaction vessel, make the separated resin circulate to the reaction vessel, and keep the amount of the resin in the reaction vessel constant. The use of this pipe, however, possibly entails such problems as induce stagnation of resin within the pipe, decrease the amount of the resin circulated thereby to the reaction vessel, cause the pipe to block, and even suffer the resin to flow out into the next step of the process.

This invention, therefore, aims to provide a method for producing an ester to solve the technical problems incurred during the separation for removal of the by-produced water. More specifically, this invention aims to provide a method for the production of the unsaturated aliphatic ester, which method is capable of efficiently producing the ester of high quality as preventing the polymerization which may well be called a prime cause of the technical problems.

SUMMARY OF THE INVENTION

The present inventors, as a result of pursuance diligent study of solving the problems mentioned above and search a method which is capable of efficiently producing the unsaturated carboxylic ester of high quality, have discovered that it is made possible, by adjusting the temperature of the reaction solution and the temperature of a heat source supplied by a heating means in respectively specified ranges and by controlling the reaction time within a prescribed duration, for example, to prevent the occurrence of a polymer on the inner wall of the reaction vessel, allow the catalyst to be uniformly stirred in the reaction solution, and consequently increase the conversion ratio of the esterification. This invention has been perfected as a result.

According to this invention, by adjusting the temperature of the reaction solution and the temperature of the outer periphery of the reaction vessel heated by a heating means in the specified ranged respectively, it is made possible to prevent the occurrence of a polymer on the inner wall of the reaction vessel and preclude the loss of the raw material compound.

BRIEF DESCRIPTION OF THE DRAWING

FIG. 1 is a schematic diagram depicting the construction of an apparatus to be used for the method by this invention for the production of the unsaturated carboxylic ester.

DESCRIPTION OF THE PREFERRED EMBODIMENT

This invention concerns a method for the production of the unsaturated carboxylic ester by the supply of the unsaturated carboxylic acid and the aliphatic alcohol into a reaction vessel equipped with a heating means on the outer periphery of the vessel, which comprises the difference between the temperature of the outer periphery of the reaction vessel heated by said heating means and the average temperature of the reaction solution in the reaction vessel being not higher than 80° C. Now, a preferred embodiment of this invention will be described below with reference to FIG. 1. In the diagram of FIG. 1, F denotes a raw material feeding port, G a molecular oxygen-containing gas, 1 a reaction vessel, 2 an agitating element, 3 a molecular oxygen-containing gas supply nozzle, 4 a heating jacket, 4' a heat medium supply line, 6 a clear liquid spray nozzle, 10 a resin separating tank, 11 a pump, 20 a distilling column, 21 a distillate, and 30 a next step.

The production of the unsaturated carboxylic ester by the method of this invention is started by feeding an unsaturated carboxylic acid and an aliphatic alcohol of 1–12 carbon atoms as a raw material through the raw material feeding port F to the reaction vessel 1. When the reaction of esterification uses a catalyst such as an ion-exchange resin, the use of this catalyst is accomplished by simply having the catalyst placed in advance in the reaction vessel 1. The control of the temperature for the purpose of optimizing the reaction of esterification is attained by means of the heat medium which is supplied through the heat medium supply line 4' to the heating jacket 4 covering the outer periphery of the reaction vessel 1. The solution introduced in the reaction vessel is stirred together with the catalyst by means of the agitating element 2. By this stirring, it is made possible to mix the supplied raw material uniformly into the solution, distribute the heat from the heating jacket 4 uniformly in the solution, and effect uniform dispersion of the ion-exchange resin incorporated as the catalyst in the solution. For the purpose of separating the product of esterification and the catalyst both contained in the solution of the reaction vessel, the reaction solution containing the catalyst is introduced to the resin separating tank 10 and separated therein into a slurry containing the resin and a clear liquid. As the solution of the reaction vessel is continuously transferred to the resin separating tank 10, the catalyst in the reaction vessel decreases gradually. For the purpose of cyclically using the catalyst in the reaction vessel 1, the slurry containing the resin is circulated from the bottom of the resin separating tank 10 via the pump 11 to the bottom of the reaction vessel. The clear liquid of the resin separating tank 10 is partly treated at the next step 30 for the separation of the product of esterification and partly circulated to the upper part of the reaction vessel. When this clear liquid is sprayed onto the inner wall of the gas phase part of the reaction vessel, the inner wall of the reaction vessel can be covered with the reaction solution. In the reaction vessel 1, the progress of the esterification forms water as a by-product and the presence of the by-produced water impedes the advance of the reaction of esterification. For the purpose of removing this by-produced water from the reaction vessel by distillation, the reaction vessel 1 is equipped in the upper part thereof with a distilling column 20 in order to separate the by-produced water by distillation.

As concrete examples of the unsaturated carboxylic acid which may be used in this invention for the production of the unsaturated carboxylic ester, such polymerizable unsaturated carboxylic acids as an acrylic acid, a methacrylic acid, a crotonic acid, an isocrotonic acid, a fumaric acid, a maleic acid, an itaconic acid, a benzoic acid, a phthalic acid, an isophthalic acid, and a terephthalic acid may be cited. Among other unsaturated carboxylic acids mentioned above, an acrylic acid and a methacrylic acid can be applied particularly advantageously as raw material compounds for the formation of corresponding esters with the aliphatic alcohol. Because the acrylic acid and the methacrylic acid in themselves and the esters thereof with the aliphatic alcohol are possessed of the polymerizable property.

The aliphatic alcohols which can be used in this invention are linear or branched monovalent, divalent, or polyvalent alcohols of 1–12carbon atoms. Monovalent alcohols include methanol, ethanol, propanol, n-butanol, t-butanol, isobutanol, pentanol, hexanol, heptanol, octanol, isooctanol, nonanol, decanol, undecanol, dodecanol, and 2-ethylhexyl alcohol, for example. Divalent alcohols include ethylene glycol, diethylene glycol, and triethylene glycol, for example. Polyvalent alcohols include glycerol, for example.

As regards the unsaturated carboxylic acids to be used as raw materials in the method of this invention, the unsaturated carboxylic acids mentioned above may be used either singly or in the form of a mixture of two or more members. The mixing ratio of the components of this mixture may be selected from an arbitrary range.

The mixing ratio of the aforementioned raw materials to be used in the method of this invention is stoichiometrically 1:1. Though actually it does not need to be particularly limited so long as it falls into the range in which the esterification of an aliphatic alcohol with the unsaturated carboxylic acid proceeds efficiently, it is generally permissible to use the two raw materials in an excess amount for accelerating the esterification. From the standpoint of ensuring purification of the target product of esterification, it prefers to use two materials having a lower boiling point in excess amount for facilitating separation by distillation.

This invention is characterized by using a reaction vessel which is equipped with a heating means on the outer periphery thereof and limiting the difference between the temperature of a heat source supplied by the heating means (temperature of the outer periphery of the reaction vessel)

and the average temperature of the solution in the reaction vessel heated by the heating means to not higher than 80° C. When the temperature of the heat source is heightened, the increase is at an advantage in permitting a decrease in the heating surface area and a reduction in the temperature increasing time and is nevertheless at a disadvantage in easily inducing polymerization on the inner wall of the reaction vessel and eventually degrading the efficiency of production. Particularly, when the heat source temperature supplied from the heating means equipped with the outer periphery of the reaction vessel is made to exceed the average temperature of the solution higher than 80° C. for the purpose of securing the solution temperature, since the inner wall of the reaction vessel reaches an elevated temperature exceeding the average temperature of the reaction solution by higher than 80° C., such an polymerizable substance as a polymerizable unsaturated carboxylic acid which has contacted to the inner wall will be stuck fast thereon by the heat of the inner wall and will be induced to polymerize quickly. The balance between the temperature of the reaction solution and the heat source supplied from the heating means, therefore, proves important. Concerning the heating of the solution in the reaction vessel, however, absolutely no consideration has been heretofore paid to the difference in temperature between the solution and the heat source. When the raw material and the product are both formed of such polymerizable substances as, for example, polymerizable unsaturated carboxylic acids, therefore, it has been necessary to lower the temperature supplied from the heating means at the sacrifice of the efficiency of production or to give a periodic cleaning to the interior of the reaction vessel while keeping the vessel at an elevated temperature. In this invention, by limiting the difference between the temperature of the reaction solution and the temperature of the outer periphery of the reaction vessel heated by the heating means to not more than 80° C., it is made possible to attain a highly effective decrease of the polymer heretofore suffered to adhere in a large amount on the inner wall of the reaction vessel. This temperature limitation further enables the efficiency of production of the unsaturated carboxylic ester to be enhanced highly efficiently. The temperature of the outer periphery of the the reaction vessel is higher than the average temperature of the reaction solution and the difference between the average temperature of the solution and the temperature of the outer periphery of the reaction vessel heated by the heating means is preferably in the range of 10–75° C. and more preferably in the range of 15–70° C. If the temperature difference falls short of 10° C., the shortage will render the operation uneconomical by entailing an increase in the heating surface area necessary for heating the reaction solution.

During the process of the esterification, the average temperature of the relevant reaction solution is retained constantly at a level which is optimum for the reaction. In the case of the esterification of such an unsaturated carboxylic acid and aliphatic alcohol as mentioned above, for example, the reaction of the esterification is generally carried out with the temperature of the reaction solution retained constantly in the range of 50–150° C. The reaction of esterification by-produces water and the reaction solution, therefore, is heated to remove the by-produced water. In this case, the temperature of the solution in the reaction vessel is generally in the range of 20–150° C., preferably in the range of 60–140° C., and particularly preferably in the range of 70–120° C. For this invention, incidentally it suffices to limit the difference between the temperature of the outer periphery of the reaction vessel which is heated by the heating means and the average temperature of the reaction solution in the reaction vessel to not higher than 80° C. The temperature of the reaction solution itself does not matter. The temperature of the reaction solution, therefore, is only required to be so selected as to suit best the kinds and concentrations of the raw materials, the kind of the catalyst to be used, and the presence or absence of the addition of an azeotropic solvent, for example.

Though the heating means to be used in this invention may be any of the devices embodying the known inventions, the use of a heating jacket proves advantageous for this invention from the viewpoint of ensuring uniform mixing of the solution in the reaction vessel. Further, the method for heating the heating jacket does not need to be particularly limited. The heating jacket may be heated to a stated temperature by supplying steam thereto.

Moreover, this invention regards the difference between the average temperature of the reaction solution and the temperature of the heating means as the key to the problem of efficiently preventing the occurrence of a polymer which is ascribed to the heating means equipped on the outer peripheral of the reaction vessel. Optionally, the reaction vessel may have equipped thereto a preheater for heating in advance such raw material compounds as the unsaturated carboxylic acid and the aliphatic alcohol and the solvent to be used for the reaction solution.

Incidentally, when the heating jacket equipped on the outer periphery of the reaction vessel is used as the heating means, the total amount of the raw material compounds, i.e. the unsaturated carboxylic acid and the aliphatic alcohol, which are introduced to the reaction vessel may suit the case of performing the reaction of esterification in the reaction vessel filled completely to capacity or the case of performing the reaction of esterification in the reaction vessel holding the reaction solution in such an amount as to permit formation of a gas phase in the upper part thereof. On the other hand, it is not proper for the heating jacket to cover the reaction vessel wholly. Particularly when the gas phase is formed in the reaction vessel as mentioned above, the reaction solution adhering on the inner wall of the gas phase in the reaction vessel is easily polymerized by the heat from the exterior of the reaction vessel. Thus, the heating jacket is preferred to cover the bottom of the reaction vessel and rise from the bottom to a height in the range of 65–95%, preferably in the range of 70–90%, and particularly preferably in the range of 75–85%, of the height of the body of the reaction vessel. If the height falls short of 65%, the shortage will be at a disadvantage in requiring the amount of the heat source supplied for heating the solution to increase excessively. Conversely, if this height exceeds 95%, the excess will be at a disadvantage in rendering it difficult to adjust the liquid level of the reaction solution at a position proper for the reaction.

This invention, when allowing the gas phase to form in the upper part of the reaction vessel, prefers the liquid level of the reaction solution during the course of the operation to rise above the upper edge of the heating jacket because this higher liquid level can effectively prevent the solution adhering on the inner wall of the reaction vessel from undergoing polymerizing. In this case, the liquid level at rest of the solution in the reaction vessel is preferred to rise from the upper edge of the heating jacket to a height in the range of 0–500 mm, preferably in the range of 100–400 mm, and particularly preferably in the range of 200–300 mm. If the liquid level rises to a height exceeding 500 mm, the excess will be at a disadvantage in entailing an expansion of the difference between the temperature of the reaction solution in the reaction vessel and the inner temperature of the heating jacket.

This invention allows addition of a catalyst for the reaction of esterification. When this catalyst happens to be an ion-exchange resin, the reaction solution requires to be stirred for the purpose of uniformly dispersing the catalyst therein and therefore entails the splashing from the open surface thereof in consequence of the physical operation of stirring. The splashing from open surface of the reaction solution in the reaction vessel occurs particularly when the boiling state is maintained therein for the purpose of removing the water by-produced by the reaction of esterification mentioned above. It has been ascertained in the present invention that when the reaction vessel to be used is given an inside diameter in the range of 0.7–1.4 based on the height of the body of the reaction vessel taken as 1, the splashing from the reaction solution from the open surface thereof is effectively repressed and polymerization on the inner wall of the reaction vessel is prevented. Furthermore, this limitation of the inside diameter is fully effective in removing the by-produced water without degrading the ratio of esterification.

The solution in the reaction vessel is not mixed fully satisfactorily when the ratio of the height of the body of the reaction vessel to the inside diameter of the reaction vessel is unduly large or unduly small. When the ratio of the height to the inside diameter is unduly small, the splashing of the solution occurs more readily because of a decrease in the cross section of the reaction vessel or the area of vaporization. Conversely, when the ratio is unduly large, since the area of the inner wall of the reaction vessel which is exposed to the gas phase increases, the possibility of the adhering solution undergoing polymerization in the affected portion increases. More favorably, the ratio of the height of the body of the reaction vessel to the inside diameter of the reaction vessel is so fixed that the inside diameter of the reaction vessel may fall into the range of 0.8–1.3, particularly preferably in the range of 0.9–1.2, based on the height of the body of the reaction vessel taken as 1. So long as the ratio of the height of the body of the reaction vessel to the inside diameter of the reaction vessel falls into the range specified above, the polymerization on the inner wall of the reaction vessel can be effectively repressed even when the stirring is effected by the known mixing means such as, for example, the stirring by the use of a stirring device or the blowing of a gas through the bottom of the reaction vessel.

The reaction vessel may be additionally equipped in the bottom thereof with a nozzle for supplying a molecular oxygen-containing gas and consequently enabled to utilize the molecular oxygen-containing gas for preventing polymerization. When the inner wall of the reaction vessel suffers adhesion of the reaction solution, the supply of the molecular oxygen-containing gas directed to the inner wall can prevent the polymerization at the relevant site of the inner wall. For the purpose of preventing the polymerization on the entire inner wall, it becomes necessary to have the plurality of such nozzles equipped on the inner wall. In this case, since the molecular oxygen-containing gas can be supplied to the gas phase uniformly, the supplying the molecular oxygen-containing gas from the bottom of the reaction vessel is preferred. As the molecular oxygen-containing gas for supply to the solution in the reaction vessel, the air of the atmosphere is available besides a pure oxygen gas. The molecular oxygen-containing gas has only to be supplied via the bottom of the reaction vessel and the place of supply or the number of places of supply are not concerned. It may be sufficient for the method to introduce the gas from a part central bottom of the vessel.

This invention concerns a method for producing the unsaturated carboxylic ester by the use of a specific reaction vessel. This production may be carried out either continuously or batchwise. The continuous production is implemented by continuously supplying the raw material compounds, i.e. the unsaturated carboxylic acid and an aliphatic alcohol, together with a catalyst which is used optionally to the reaction vessel and heating to a prescribed temperature the reaction solution in the reaction vessel with a heat source obtained from a heating means equipped on outside the reaction vessel thereby enhancing the reaction of esterification.

When the method of this invention for the production of the unsaturated carboxylic ester is carried out batchwise, the batchwise production is effected by introducing the unsaturated carboxylic acid and the aliphatic alcohol mentioned above to the reaction vessel, optionally adding a catalyst thereto, elevating the temperature of the solution in the reaction vessel with a heating means equipped on the outer periphery of the reaction vessel to a prescribed level, and retaining the temperature at this level thereby enhancing the reaction of esterification. As the esterification proceeding, it entails formation of by-produced water. After the reaction of esterification has reached equilibrium, the reaction solution may be withdrawn from the reaction vessel and the by-produced water separated from the withdrawal solution. Otherwise, similarly to the case of the continuous production, the by-produced water may be separated and removed from the reaction vessel simultaneously with the advance of the reaction by means of a distilling column which is equipped with the reaction vessel. Incidentally, even the method of batchwise production is at an advantage in permitting production of the unsaturated carboxylic ester while preventing the polymerization on the inner wall of the reaction vessel because it has the upper end part of the solution in the reaction vessel rise above the upper end part of the heating means.

This invention, when necessary, permits addition of a polymerization inhibitor to the reaction system, namely the reaction solution having incorporated therein the raw material compounds, without reference to the discrimination of the reaction vessel between the continuous type and the batchwise type. The reason for this addition is that the use of the polymerization inhibitor results in effectively preventing the aliphatic alcohol and the unsaturated carboxylic acid which are the raw materials and the product of the esterification of the acid from polymerizing. The polymerization inhibitor which can be used in this invention does not need to be particularly limited but may be selected from among the known polymerization inhibitors. Among other conceivable polymerization inhibitors, phenothiazine and hydroquinone monomethyl ether are particularly advantageously usable. These polymerization inhibitors may be used either singly or in the form of a combination of two or more members.

The amount of the polymerization inhibitor to be used is in the range of 0.001–1 weight %, preferably in the range of 0.001–0.1 weight %, based on the amount of the unsaturated carboxylic acid charged in the reaction system. If the amount of the polymerization inhibitor to be used falls short of 0.001 weight %, the shortage will be at a disadvantage in preventing the polymerization inhibitor from manifesting the ability thereof to inhibit polymerization fully satisfactorily and rendering it difficult to prevent effectively the unsaturated carboxylic acid as a raw material, the product of esterification, or the mixture thereof from yielding to polymerization. If the amount of the polymerization inhibitor to be used exceeds 1 weight %, the excess will be at a disadvantage in impairing the product of esterification in quality and performance because of an unduly large residue of polymerization inhibitor and meanwhile failing to bring the economical merit of proportionately adding to the effect of the inhibitor.

This invention, when necessary, permits addition of a catalyst to the reaction system for the esterification. The catalyst to be used for the addition does not need to be particularly limited but may be properly selected, depending on the kind of ester to be produced and the reaction conditions to be adopted, so as to suit the purpose. Such catalysts are generally known in the two kinds, heterogeneous catalysts and homogeneous catalysts.

As concrete examples of the heterogeneous catalysts which are advantageously used herein, such commercially available ion-exchange resins which are produced by Rohm and Haas Company and sold under trademark designations of "Amberlite IR-116," "Amberlite IR-120," "Duolite DX900," and "Duolite DX2001," produced by Mitsubishi Chemical Co., Ltd. and sold under trademark designations of "Diaion PK-208," "Diaion PK-228," and "Diaion SK-1," produced by the Dow Chemical Company and sold under trademark designation of "Dowex HCR-W2," and produced by Sumitomo Chemical Industry Co., Ltd. and sold under trademark designation of "Duolite C-26" may be cited.

As concrete examples of the homogeneous catalysts which are usable herein, sulfuric acid, methasulfonic acid, benzene sulfonic acid, paratoluene sulfonic acid, xylene sulfonic acid, and phosphoric acid may be cited.

The reaction time for the esterification is preferred to be in the range of 0.5–3 hours. The residence time of the reaction solution in the reaction system is in the range of 0.5–3 hours, preferably in the range of 0.6–2.5 hours, and particularly preferably in the range of 0.8–2.0 hours. If the residence time falls short of 0.5 hour, the shortage will be at a disadvantage in requiring the reaction temperature to be elevated for the purpose of retaining the rate of reaction at a prescribed level and consequently entailing an addition to the amount of the by-product to be formed and a decrease in the yield of the product. Conversely, if the retention time exceeds 3 hours, the excess will be at a disadvantage in suffering the unsaturated carboxylic acid and the ester thereof to undergo dimerization readily. These durations may be properly selected in the respective ranges mentioned above, depending on the temperature in the reaction vessel of the reaction solution incorporating therein the raw material compounds, the kind of catalyst to be used, and the method for the removal of the by-produced water.

In this invention, when an ion-exchange resin is added as a catalyst to the reaction vessel, the ion-exchange resin mingles in the reaction solution with the unsaturated carboxylic ester which is the target product and departs from the reaction vessel together with the target product during the extraction of this product. The solution containing the catalyst, therefore, is preferred to be introduced into a resin separating tank and separated therein into a slurry containing the resin and the clear liquid. Then, by cycling the slurry containing the ion-exchange resin to the reaction vessel, the ion-exchange resin can be easily reuse.

The bends formed in the pipe laid for circulating the slurry containing the ion-exchange resin to the reaction vessel are preferred to have an inside radius of curvature of not less than three times the inside diameter of the pipe. The reason for using this radius of curvature in each of the bends in the pipe is that the interior of the pipe can be efficiently prevented from inducing polymerization because the reaction solution is circulated to the reaction vessel without stagnating in the pipe. Generally, the fluidity of a fluid is affected by such phenomena as viscoelasticity, stress relaxation, creep, elastic lag, plastic flow, and thixotropy. Even one same fluid has the fluidity thereof varied by the temperature and the velocity of the fluid. In this invention, the slurry containing the resin and withdrawn from the resin separating tank contains the unsaturated carboxylic acid, an aliphatic alcohol, and the unsaturated carboxylic ester, and a solvent, a polymerization inhibitor, and an ion-exchange resin which are added as occasion demands. When the slurry is circulated to the reaction vessel by the pump, the bends having a radius of curvature of not less than three times the inside diameter of the pipe can prevent from stagnating the slurry and fracturing the ion-exchange resin contained the slurry. When any of the bends in the pipe has a smaller radius of curvature, the pipe tends to induce stagnation or adhesion of a resin in the bend and consequently entails such disadvantages as necessitating an increase in the flow rate of the slurry, rendering the resin readily fracturable, and suffering the fractured resin to degrade the yield of production. It has been ascertained by the present inventors that when the radius of curvature is not less than three times the inside diameter of the pipe, the problems mentioned above are solved because the resistance to the fluid is decreased and the stagnation of the flow is eliminated. This effect excels particularly when the resin concentration in the slurry is in the range of 20–70 volume %, preferably in the range of 25–65 volume %, and especially preferably in the range of 30–60 volume %. The flow velocity of the slurry in this case is preferably in the range of 0.5–3.0 m/sec, more preferably in the range of 0.8–2.5 m/sec, and particularly preferably in the range of 1.0–2.0 m/sec. Though the viscosity of the slurry does not need to be particularly limited, it is preferably not more than 20 cP, more preferably not more than 15 cP, and particularly preferably not more than 10 cP.

The clear liquid which is formed after the resin has been precipitated in the resin separating tank is preferred to be circulated, at least partly, to the inner wall of the gas phase in the reaction vessel. This circulation is particularly preferred to be effected by a procedure of spraying the clear liquid on the inner wall of the gas phase in the reaction vessel. This procedure is at an advantage in easily allowing the splash of the reaction solution adhering to the gas phase part of the reaction vessel to flow down into the solution and consequently precluding the otherwise inevitable occurrence of polymerization in the gas phase part. Particularly when the raw material compounds and the solvent are continuously supplied to the reaction vessel and the reaction solution is continuously supplied to the resin separating tank, the reaction vessel tends to give rise to a gas phase part therein as described above and consequently induce adhesion of a polymer on the inner wall of this gas phase part. When a liquid from an external source is sprayed onto the inner wall in this case, this spray has the possibility of lowering the rate of the reaction of esterification. By spraying the clear liquid comprising the unsaturated carboxylic ester as raw material compounds, it is made possible to produce the ester of the unsaturated carboxylic acid while avoiding retardation of the rate of the reaction of esterification and preventing adhesion of a polymer as well. This spraying is accomplished by laying a pipe for interconnecting the resin separating tank and the reaction vessel for esterification, forming in the pipe an inlet for introducing the clear liquid, and providing this inlet at the leading end thereof with such a spray as enables the clear liquid to be directed toward the inner wall of the reaction vessel. The leading end part which is shaped like a spray is only required to be so equipped that the spray of the clear liquid may provide the gas phase part of the inner wall in the reaction vessel. The leading end part does not need to be used solely. A plurality of such leading end parts may be installed as spaced. The gas phase part for the sake of this spray does not need to be particularly limited. The spray may be initiated not only from the lateral wall of the reaction vessel but also from the upper part of the reaction vessel. Incidentally, the clear liquid in the resin separating tank possibly has fine particles of ion-exchange resin float thereon. Thus, the port of the resin separating tank for discharging the clear liquid is preferred to be provided with a mechanism for filtering the floating particles.

Embodiments

Now, this invention will be described more specifically below with reference to working examples thereof.

EXAMPLE 1

In a cylindrical reaction vessel measuring 3100 mm in inside diameter and 3100 mm in straight body length and equipped with a Faudler vane measuring 1900 mm in diameter, the reaction of esterification of acrylic acid and n-butanol was carried out by stirring the reaction solution at an stirring speed of 40 rpm. As the catalyst for this reaction, a strongly acidic cation-exchange resin (made by Mitsubishi Chemical Industry Co., Ltd. and sold under trademark designation of "Diaion PK208") was used in a volume of 15.5 $m^3$ (in a state wetted with water). The reaction was performed under the conditions of 80° C. in reaction temperature (temperature of the reaction solution) and 20 kPa (absolute pressure) in reaction pressure. The reaction solution was heated with steam, which was supplied to a jacket coating the reaction vessel to 90% of the height of the straight body thereof. The internal pressure of the jacket was 0.2 MPa (gauge pressure) and the temperature of the outer peripheral part of the reaction vessel was about 133° C. The volume of the reaction solution was such that the liquid level in the reaction vessel was 100 mm higher than the top of the jacket and the residence time of the reaction solution in the reaction vessel was 1.5 hours. Through the nozzle equipped at the center of the bottom of the reaction vessel, air of an amount of 0.2 volume % based on the amount of the steam generated in the reaction vessel was supplied.

The apparatus was stopped five months after the start of the operation. When the interior of the reaction vessel was inspected, practically no sign of the formation of a polymer was detected.

COMPARATIVE EXAMPLE 1

The operation of the apparatus was carried out by following the procedure of Example 1 while changing the pressure of the steam in the jacket equipped to the reaction vessel to 0.5 MPa (gauge pressure) and the temperature of the outer periphery of the reaction vessel to about 159° C.

About two months after the start of the operation, the apparatus was stopped on account of the polymerization on the inner wall above the liquid level of the reaction solution.

EXAMPLE 2

In the reaction vessel of Example 1 equipped thereto a resin separating tank 1700 mm in inside diameter and 2000 mm in length, the reaction was carried out while separating the reaction solution into a slurry containing the resin and a clear liquid. The flow rate of the reaction solution supplied from the reaction vessel to the resin separating tank was 112 $m^3$/h. The clear liquid was withdrawn at a rate of 18 $m^3$/h and the slurry liquid was circulated at a rate of 1.5 m/sec to the reaction vessel. The slurry concentration in the slurry liquid withdrawn from the resin separating tank was 25 vol. %.

A stainless steel pipe 150 mm in diameter was used as the flow path for the slurry circulated from the resin separating tank to the reaction vessel. Since the bends formed in this pipe were given a radius of curvature of 600 mm, the interior of the pipe was free from such trouble as blockage.

EXAMPLE 3

The reaction of esterification of acrylic acid and 2-ethylhexyl alcohol was carried out by using a strongly acidic cation-exchange resin (made by Mitsubishi Chemical Industry Co., Ltd. and sold under trademark designation of "Diaion PK208") in a volume of 10 $m^3$ (in a state wetted with water) under the conditions of 85° C. in reaction temperature (temperature of the reaction solution) and 10 kPa (absolute pressure) in reaction pressure. The liquid fed to the reaction vessel was heated to 80° C. by a preheater. The temperature of the reaction solution was also elevated with the steam supplied to the jacket equipped to the reaction vessel. The internal pressure of the jacket was 0.35 MPa (gauge pressure) and the temperature of the outer periphery of the reaction vessel was about 148° C. The reaction solution was supplied from the reaction vessel to the resin separating tank was supplied at a rate of 2 m/sec.

From the resin separating tank, the clear liquid was discharged at a rate of 7 $m^3$/h and the slurry containing the resin was discharged at a rate of 50 $m^3$/h. The slurry was circulated to the reaction vessel. Of the clear liquid, the part of 1 $m^3$/h was circulated to be used for spraying the inner wall of the reaction vessel and the remainder thereof was supplied to the next step.

When the operation was continued under the conditions mentioned above, no polymer was generated in the reaction vessel even after the elapse of four months following the start of the operation.

COMPARATIVE EXAMPLE 2

The operation was performed by the following procedure of Example 3 while omitting the use of a preheater and supplying the feed liquid at 40° C. The internal pressure of the jacket equipped to the reaction vessel was 0.55 MPa (gauge pressure) and the temperature of the outer periphery of the reaction vessel rose to about 162° C. Two months after the start of the operation, the apparatus was stopped on account of the generation of a polymer on the inner wall above the liquid level of the reaction solution.

What is claimed is:

1. A method for the production of an unsaturated carboxylic ester by the supply of an unsaturated carboxylic acid and an aliphatic alcohol into a reaction vessel equipped with a heating means on the outer periphery of the vessel, which comprises the steps of:

heating a reaction solution obtained with said heating means, said heating means comprises a heating jacket equipped on the outer periphery of said reaction vessel, the liquid level of the reaction solution during the course of the operation is allowed to rise above the upper edge of the heating jacket, the reaction solution is heated in the range of about 50° C. to about 150° C.; and keeping the difference between the temperature of the outer periphery of the reaction vessel heated by said heating means and the average temperature of the reaction solution in the reaction vessel in the range of 10° C. to 75° C.

2. A method according to claim 1, wherein a molecular oxygen-containing gas is supplied to said reaction vessel through a bottom thereof.

3. A method according to claim 1, wherein said reaction vessel allows the presence therein of an ion-exchange resin as a catalyst.

4. A method according to claim 1, wherein the inside diameter of said reaction vessel is 0.7–1.4 times the height of the body of said reaction vessel.

5. A method according to claim 3, which comprises the steps of introducing said ion-exchange resin in said reaction vessel together with the reaction solution into a resin separating tank, separating the contents of said resin separating tank into a slurry containing said ion-exchange resin and a clear liquid containing the unsaturated carboxylic ester, and circulating said slurry to said reaction vessel by the use of a pipe having a radius of curvature of not less than three times the inside diameter of said pipe.

6. A method according to claim 5, wherein said slurry is circulated at a flow rate in the range of 0.5–3.0 m/sec.

7. A method for the production of an unsaturated carboxylic ester by the supply of an unsaturated carboxylic acid and an aliphatic alcohol into a reaction vessel equipped with a heating means on the outer periphery of the vessel, said reaction vessel allows the presence therein of an ion-exchange resin as a catalyst which comprises the steps of:

keeping the difference between the temperature of the outer periphery of the reaction vessel heated by said heating means and the average temperature of the reaction solution in the reaction vessel to not higher than 80° C.;

introducing said ion-exchange resin in said reaction vessel together with the reaction solution into a resin separating tank, separating the contents of said resin separating tank into a slurry containing said ion-exchange resin and a clear liquid containing the unsaturated carboxylic ester, and circulating said slurry to said reaction vessel by the use of a pipe having a radius of curvature of not less than three times the inside diameter of said pipe, wherein at least part of said clear liquid in the resin separating tank is circulated on the inner wall of the gas phase part in the reaction vessel.

8. A method according to claim 7, wherein the circulation to the reaction vessel consists in spraying said clear liquid on the inner wall of the gas phase part in the reaction vessel.

* * * * *